United States Patent [19]

Duggan et al.

[11] Patent Number: 4,692,426

[45] Date of Patent: Sep. 8, 1987

[54] PHOSPHITE-PROMOTED RUTHENIUM-COBALT CATALYSTS FOR THE DEALKOXYHYDROXYMETHYLATION OF ACETALS TO FORM GLYCOL ETHERS

[75] Inventors: D. Michael Duggan, Drexel Hill; James E. Lyons, Wallingford; Harry K. Myers, Jr., Cochranville, all of Pa.

[73] Assignee: Sun Refining and Marketing Company, Philadelphia, Pa.

[21] Appl. No.: 901,861

[22] Filed: Aug. 29, 1986

Related U.S. Application Data

[63] Continuation-in-part of Ser. No. 783,971, Oct. 2, 1985, abandoned, which is a continuation-in-part of Ser. No. 623,059, Jun. 21, 1984, abandoned.

[51] Int. Cl.$^4$ ............................................. B01J 31/20
[52] U.S. Cl. ................................... 502/154; 502/155; 502/161; 556/12; 556/16; 568/678
[58] Field of Search ..................... 502/154, 155, 161; 556/16, 12

[56] References Cited

U.S. PATENT DOCUMENTS

| | | | |
|---|---|---|---|
| 2,525,793 | 10/1950 | Gresham et al. | 260/615 |
| 4,062,898 | 12/1977 | Dubeck et al. | 260/632 B |
| 4,308,403 | 12/1981 | Knifton | 568/678 |
| 4,317,943 | 3/1982 | Knifton | 568/678 |
| 4,346,020 | 8/1982 | Pretzer et al. | 502/161 X |
| 4,356,327 | 10/1982 | Knifton | 568/678 X |
| 4,357,477 | 11/1982 | Knifton | 502/170 X |
| 4,390,734 | 6/1983 | Knifton | 568/678 |

FOREIGN PATENT DOCUMENTS

| | | |
|---|---|---|
| 34374 | 8/1981 | European Pat. Off. . |
| 83432 | 7/1981 | Japan . |

*Primary Examiner*—Patrick P. Garvin, Sr.
*Attorney, Agent, or Firm*—J. Edward Hess; Donald R. Johnson; Stanford M. Back

[57] ABSTRACT

Ruthenium-cobalt carbonyl catalysts which have been promoted with an organophosphite effectively catalyze the dealkoxyhydroxymethylation of aldehyde acetals to form glycol monoethers. Methylal, for example, may be reacted with syngas, i.e., CO and $H_2$, in the presence of this phosphite-promoted ruthenium carbonyl cobalt catalyst to form the monomethyl ether of ethylene glycol. In a like manner acetaldehyde may be converted to the corresponding propylene glycol monoether. The process may advantageously be carried out with high yields and selectivities in the presence of a polar or non-polar organic solvent in combination with the catalyst system of this invention.

The invention is also directed to certain of the organophosphite-promoted cobalt and ruthenium-cobalt carbonyl catalyst systems per se.

24 Claims, No Drawings

PHOSPHITE-PROMOTED RUTHENIUM-COBALT CATALYSTS FOR THE DEALKOXYHYDROXYMETHYLATION OF ACETALS TO FORM GLYCOL ETHERS

CROSS-REFERENCE TO RELATED APPLICATION

The application is a continuation-in-part of Ser. No. 783,971, filed Oct. 2, 1985 and now abandoned, which in turn is a continuation-in-part of Ser. No. 623,059, filed June 21, 1984 and now abandoned.

BACKGROUND OF THE INVENTION

1. Scope of the Invention

This invention relates to the dealkoxyhydroxymethylation of aldehyde acetals. More particularly, it relates to a novel process for the dealkoxyhydroxymethylation of certain dialkyl-, dicycloalkyl-, diaryl- or cyclic-aldehyde acetals by reacting said acetals with syngas, i.e., hydrogen and carbon monoxide, in the presence of novel organophosphite-promoted ruthenium-cobalt carbonyl catalysts or phosphite-cobalt catalysts, to form the corresponding glycol monoethers. Still more particularly, it relates to the catalysts per se and methods for preparing the same. In a further embodiment, it is also directed to a process for the dealkoxyhydroxymethylation of acetals in the presence of a solvent in combination with the aforedescribed catalyst system. The acetals described herein may be prepared separately or formed in situ from the corresponding aldehyde and alcohol precursors.

The glycol ethers described herein encompass known classes of compounds having various uses, as for example as jet fuel additives, cleaners, coatings solvents, intermediates in the production of certain diphthalates, and the like.

2. Description of the Prior Art

One current well-known method of manufacturing glycol monoethers such as monoalkyl ethers consists of reacting ethylene oxide with the alcohol corresponding to the desired alkyl ether, employing various known catalyst systems.

Alternatively, the cobalt-catalyzed reaction of aldehydes or their dialkyl acetals with syngas, i.e., the carbon monoxide-hydrogen mixture, to form the corresponding glycol ether is also described in the art. Thus, for example, a method of making ethylene glycol ethers is described in U.S. Pat. No. 2,525,793 which employs cobalt oxide to catalyze the reaction of methylal with syngas to provide a reaction mixture which, after hydrogenation over nickel, gives relatively uneconomical conversions on the order of 25-33%.

Numerous attempts have been made to obtain more practical yields of glycol ethers from aldehydes or their dialkylacetals. A number of promoters have been used in conjunction with various cobalt catalysts in an effort to improve reaction rates and product yields. U.S. Pat. No. 4,062,898, for example, discloses a ruthenium chloride-promoted cobalt iodide catalyst which hydrocarbonylates formaldehyde dimethylacetal (methylal) to ethylene glycol monomethyl ether, (EGMME) in yields of 10% or less. The reaction temperature required is 185° at 20 atm. or above. A second method, described in Jpn. Kokai Tokkyo Koho 81 83,432, (1981) uses substantial quantities of 2,4,6-collidine or similar aromatic amines to promote the cobalt carbonyl-catalyzed hydrocarbonylation of methylal in benzene as a solvent. The reaction of methylal with highly pressurized syngas in this process at 190° C. for 10 hours gave 44% selectively to EGMME at 98% conversion. A further patent, Euro. Pat. Appln. No. 34,374 (1981) uses both iodine and triphenyl or tricyclohexylphosphine together with $RuCl_3 \cdot H_2O$, to promote the $Co(Ac)_2 \cdot 4H_2O$-catalyzed hydrocarbonylation of methylal using 3000 psig of syngas, temperatures of between 150° and 175° C. to obtain results nearly comparable to those of the Japanese. U.S. Pat. No. 4,346,020 to Pretzer et al teaches a four-component catalyst comprising a combination of certain cobalt and ruthenium compounds and a Group VA compound. However, because that patent addresses a fundamentally different reaction, for producing ethanol, it is essential that an additional component be present, e.g. an iodine promoter for said ethanol synthesis from methanol.

More recently, Knifton has found that cobalt carbonyl promoted with a Group VIB donor ligand catalyzes the hydrocarbonylation of an aldehyde in an alcohol to make ethylene glycol monoethers; U.S. Pat. No. 4,308,403. Yields of ethylene glycol monobutyl ether (EGMBE) as high as 61 wt.% were reported in this patent. A cyclopentadienyl-ligated cobalt catalyst is also effective for these reactions giving glycol ethers in up to 54% yield; U.S. Pat. No. 4,317,943.

Propylene glycol monoalkyl ethers are formed by contacting high pressure mixtures of carbon monoxide and hydrogen with either an acetal or an aldehyde and an alcohol using a cobalt catalyst promoted with a tin- or germanium-containing compound; U.S. Pat. No. 4,356,327. Yields of glycol ethers up to 31 wt.% were reported in this patent. Ethylene glycol ethers were also formed from a formaldehyde acetal or formaldehyde and an alcohol using tin or germanium promoters for cobalt carbonyl; U.S. Pat. No. 4,357,477. The highest glycol ether yield (EGMBE) was 53% in this case. Finally, propylene glycol monoalkyl ethers were formed by hydrocarbonylation of acetaldehyde acetals or acetaldehyde and alcohols using rhodium, ruthenium or nickel compounds to promote ether cobalt carbonyls or cobalt compounds having group V ligand systems attached. Glycol ether yields up to 28 wt.% were realized when these promoters were used; Knifton, U.S. Pat. No. 4,390,734 (1983).

Thus, the use of various promoters for the cobalt-catalyzed hydrocarbonylation of aldehydes or acetals has resulted in glycol ether yields of from 10-61 wt.%, depending on the glycol ether produced. The highest reported yield of EGMME is 44%, of EGMBE is 61% and propylene glycol monoethyl ether, PGMEE is 28%.

SUMMARY OF THE INVENTION

In accordance with the present invention, there is provided an improved process for the reaction of certain dialkyl-, dicycloalkyl-, diaryl-, or cyclic-aldehyde acetals or their aldehyde-alcohol precursors with syngas in the presence of novel organophosphite-promoted ruthenium-cobalt carbonyl and cobalt carbonyl catalyst systems to form the corresponding glycol monoethers. This reaction, which may best be described as the dealkoxyhydroxymethylation of an acetal, formed separately or in situ by the known reaction of an aldehyde with an alcohol, may be depicted by the following general reaction scheme:

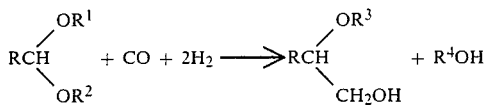

wherein R is hydrogen, alkyl, cycloalkyl, or aryl; $R^1$ and $R^2$, which may be the same or different, are alkyl, cycloalkyl, aryl, and taken together may form a cyclic acetal; $R^3$ is alkyl, cycloalkyl, aryl, or an hydroxy-substituted hydrocarbon moiety; and $R^4$ is alkyl, cycloalkyl, or aryl, coresponding to whichever $R^1$ or $R^2$ group is displaced. In the case where cyclic acetals are employed, however, no alcohol by-product is formed.

Examples of $R^1$, $R^2$, $R^3$ or $R^4$ alkyl, cycloalkyl, and aryl groups which may be employed include those containing such substituted or unsubstituted groups as:

(a) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(b) substituted or unsubstituted cycloalkyl groups, preferably those having from about 5 to about 20 carbon atoms, such as cyclopentyl, cyclohexyl, cycloheptyl, 3-methylcyclopentyl, 3-butylcyclohexyl, 3-methylcyclopentyl, 3-butylcyclohexyl, cyclooctyl, adamantyl, decalyl, 3-phenylcycloheptyl and the like; and (c) substituted or unsubstituted aryl groups, preferably those having from 6 to about 20 carbon atoms such as benzyl, phenyl, naphthyl, fluoranthyl, tetralyl, tolyl, ethylphenyl, cumyl, anisyl, chlorophenyl, and the like.

It will be understood that when $R^1$ and $R^2$ in the foregoing reaction scheme are different, the resulting products will actually be mixtures of the corresponding glycol ethers and alcohols. It will also be understood, as mentioned above, that $R^1$ and $R^2$ may be joined by one or more bridging atoms to form a cyclic acetal, in which case, under the conditions of this reaction the heterocyclic ring will cleave at a carbon-oxygen bond of the acetal moiety, and hydroxymethylate, thereby forming a dihydroxy compound, i.e. an hydroxy-substituted glycol ether.

The present process, using the novel catalysts of this invention, provides an improvement over the methods of the prior art in that these catalysts permit the reaction to be carried out under mild conditions of time and temperature, yet most surprisingly provide rates and selectivities of desired product over those obtained by the use of cobalt carbonyl alone, or the ruthenium carbonyls alone.

This invention is also directed to the novel organophosphite promoted ruthenium-cobalt carbonyl catalysts per se, and to methods for preparing them. As described in further detail below, this catalyst system comprises a combination of:

(a) an organophosphite promoter of the formula $P(OR')_3$, i.e., having the structure

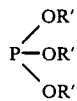

wherein each of the three R' groups, which may be the same or different, comprise any organic moieties which are inert to the conditions of the reaction, and include:
(1) hydrogen;
(2) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;
(3) substituted or unsubstituted cycloalkyl groups, preferably those having from about 5 to about 20 carbon atoms, such as cyclopentyl, cyclohexyl, cycloheptyl, 3-methylcyclopentyl, 3-butylcyclohexyl, cyclooctyl, adamantyl, decalyl, 3-phenylcycloheptyl and the like; and
(4) substituted or unsubstituted aryl groups, preferably those having from 6 to about 20 carbon atoms such as benzyl, phenyl, naphthyl, fluoranthryl, tetralyl, tolyl, ethylphenyl, cumyl, anisyl, chlorophenyl, and the like; and (b) a ruthenium-cobalt carbonyl compound, or mixture of ruthenium carbonyl and cobalt carbonyl compounds, selected from group consisting of
(1) a mixture of $Co_2(CO)_8$ and $Ru_3(CO)_{12}$;
(2) $Co_2Ru(CO)_{11}$; and
(3) a mixture of $R^5CCo_3(CO)_9$ and $Ru_3(CO)_{12}$,
wherein $R^5$ may be hydrogen; alkyl, preferably $C_{1-12}$ alkyl, and most preferably $C_{1-5}$ lower alkyl; cycloalkyl or alkyl-substituted cycloalkyl, preferably $C_{5-10}$ moieties; ; cycloalkenyl, preferably $C_{6-12}$ cycloalkenyl, such as cyclohexenyl or cyclooctenyl; alkoxy, preferably $C_{1-12}$ alkoxy, such as methoxy or propoxy; aryl or alkyl-, cycloalkyl-, alkoxy-, halo-, or cyano-substituted aryl, preferably $C_{6-20}$ moieties; or a silyl moiety of the formula $R^6{}_3Si$, wherein $R^6$ is alkyl or aryl.

In a further embodiment, it has also been found that the organophosphites $P(OR')_3$, as defined above, may satisfactorily be employed as promoters for the aforedefined cobalt catalyst, $R^5CCo_3(CO)_9$ in the absence of the ruthenium carbonyl component. Thus, for example, tricyclohexylphosphite will effectively promote $HCCo_3(CO)_9$ as a catalyst in the conversion of methylal to ethylene glycol monomethyl ether. Other combinations of phosphites and carbyne-substituted cobalt carbonyls as described above and in the examples are also useful in this process.

DESCRIPTION OF THE CATALYST SYSTEM

The novel catalysts employed in the process of this invention are readily prepared by mixing the phosphonite or phosphinite with any of the cobalt carbonyl or ruthenium-cobalt carbonyl compounds, or mixtures, set forth above. The molar ratio of organophosphite to ruthenium-cobalt carbonyl compound or mixture, or to carbyne-substituted cobalt carbonyl, is desirably in the range of 1:5 to 5:1, and preferably 1:3 to 3:1.

The organophosphite promoters are generally known compounds which are commercially available articles of commerce. Examples of such phosphites include trimethylphosphite, triethylphosphite, tributylphosphite, triphenylphosphite, trineopentylphosphite, tricyclohexylphosphite, and the like, of which the higher molecular weight trialkylphosphites are preferred.

The first of the ruthenium and cobalt carbonyl compounds which may advantageously be promoted by an organophosphite are a mixture of ruthenium carbonyl and dicobalt octacarbonyl, more specifically, triruthenium dodecarcarbonyl-dicobalt octacarbonyl mixtures. This mixture may readily be prepared by adding dicobalt octacarbonyl, (Co$_2$(CO)$_8$), with ruthenium dodecarcarbonyl, (Ru$_3$(CO)$_{12}$), in the reaction medium. The molar ratios of these two components are optimally in the range of about 10:1 to 1:10, and preferably about 5:1 to 1:5.

Alternatively, the organophosphite may be used as a promoter with the metal cluster Co$_2$Ru(CO)$_{11}$. This catalyst may be prepared by the method disclosed by Roland et al., *Angew. Chem. Int. Ed. Engl.*, 20, 679 (1981).

The third of these compounds which may be advantageously promoted with an organophosphite is a carbyne-substituted cobalt compound having the formula R$^5$CCo$_3$(CO)$_9$, wherein R$^5$ is as defined above, in combination with Ru$_3$(CO)$_{12}$. The carbyne-substituted cobalt carbonyl compounds may be prepared in accordance with the precedures taught in *Inorganic Synthesis*, Wiley-Interscience Pub., New York, Vol. 20, #53-B, pp. 226 et seq. (1980). As indicated above, this catalyst may be used with the organophosphite promotor with or without Ru$_3$(CO)$_{12}$, but more preferably with the ruthenium component. The molar ratios of these two components in the latter combination, should optimally be in the range of about 10:1 to 1:10 and preferably about 5:1 to 1:5.

In yet a further embodiment of this invention, it has been found that phosphite-substituted cobalt and ruthenium complexes having the following formulas may also be employed as catalyst in the dealkoxyhydroxymethylation reactions of this process:

$$R^5CCo_3(CO)_{9-x}(P(OR')_3)_x;$$

$$Co_2(CO)_7P(OR')_3; \text{ or}$$

$$Ru_3(CO)_{12-x}(P(OR')_3)_x$$

wherein R$^5$ and R' are as defined above, and x is an integer of from 1-3 inclusive.

These cobalt complexes may readily be prepared by the thermal displacement of the carbonyl groups of the corresponding cobalt carbonyl compounds, e.g. by heating the R$^5$CCo$_3$(CO)$_9$ with a trisubstituted phosphite such as PPh$_3$ at elevated temperature, followed, if necessary, by purification and separation by chromatography; Beurich et al, *Chem. Ber.*, 114, 2542-67 (1981); while the euthenium complexes may be prepared in a similar fashion in accordance with the procedures of *J. Organomet. Chem.*, 247, pp. 321-343 (1983).

Examples of preferred ruthenium- and cobalt-phosphite complexes include such compounds as triruthenium undecacarbonyl trineopentyl phosphite, and methyne tricobalt octacarbonyl trineopentyl phosphite.

DESCRIPTION OF THE PROCESS

The acetal dealkoxyhydroxymethylation reaction with syngas, as described above, utilizing the novel organophosphite-promoted cobalt carbonyl catalysts of this invention, may conveniently be conducted in a generally known manner whereby the desired acetal is reacted with syngas under elevated temperature and pressures for given periods of time, during which period the reaction mixture is actively stirred. In this reaction, the volume ratio of carbon monoxide to hydrogen in the syngas desirably is in the range of from about 1:5 to 5:1, and more preferably 1:3 to 3:1. Following rapid cooling, the reaction product is then recovered from the mixture in a routine manner.

In contrast to prior art reaction conditions described above, the catalysts of this invention advantageously permit the use of mild operating conditions. Thus, temperatures in the range of from about 100° to 200° C., and preferably about 125° to 175° C., pressures of from about 500 to 5000 psi, and preferably about 1000 to 3000 psi, may satisfactorily be employed. The reaction time is not critical and may range up to several hours, desirably about 1-6 hours.

The weight ratio, in grams, of phosphite promoter and catalyst, i.e., catalyst mixture to acetal, is desirably in the range of from about 1:1000-10:1, and preferably in the range of from about 1:100-1:1 in a batch reaction.

In a further embodiment of this invention, it has been found that highly advantageous effects may also be obtained in this dealkoxyhydroxymethylation process by the use of solvents with the acetal. The solvents which may be advantageously used comprise any polar or non-polar organic solvents which are inert to the conditions of the reaction. Included amongst these solvents are C$_{1-12}$ alcohols, such as methanol, ethanol, butanol, 3-ethyl-2-hexanol and the like; ethers which will not cleave under the conditions of the reaction, such as glyme, diglyme, diphenyl ether and the like; aromatics and substituted aromatics such as benzene, toluene, xylene, chlorobenzene, dichlorobenzene, anisole, and the like.

The solvents may be employed in amounts of up to 90 volume percent of the reaction mixture, and preferably in amounts of about 20 to 80 percent.

In still a further embodiment of this process, it has been found that with acylic acetals, when the reaction is carried out in an excess of an alcohol solvent, wherein the ratio of acetal to alcohol solvent is desirably in the range of from about 1:2 to 1:20, and preferably 1:5 to 1:10, and wherein the R group of the alcohol used is different from the R$^1$ and/or R$^2$ substituents on the acetal starting material, these different R groups of the alcohol will, in the course of the reaction, replace the R$^1$ and/or R$^2$ groups on the acetal in a substitution reaction, thereby resulting in a glycol monoether in which the R group of the ether moiety corresponds to the R group of the alcohol solvent.

This reaction may be illustrated by the following equation:

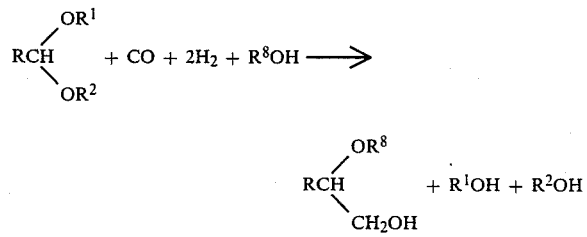

wherein R, R$^1$, and R$^2$ are as defined above, except that cyclic acetals are not included, and R$^8$ is a different alkyl, cycloakyl, or aryl group than R$^1$ and/or R$^2$, and desirably has from 1 to about 20 carbon atoms. Depending upon the length of the time the reaction is allowed to continue, intermediate mixtures of higher and lower molecular weight substituents on the acetal corresponding to both those of the R$^1$ and/or R$^2$ groups and those of the alcohol solvent will be found in the reaction product.

The acetal starting materials employed in this invention have the aforedescribed general formula, namely

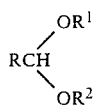

wherein the R, $R^1$ and $R^2$ are as defined above. These acetals can be prepared in a known manner, as for example as described in E. V. Dehmlav and J. Schmidt, Tetrahedron Letters, p. 95-6 (1976) B. S. Bal and H. W. Pinnick, J. Org. Chem. V44 (21), p. 3727-8 (1979) D. W. Hall, U.S. Pat. No. 3,492,356, Jan. 27 (1970), by the reaction of an aldehyde such as formaldehyde with an alcohol, or mixture of alcohols, of the general formula $R^1OH$ or $R^2OH$, where again $R^1$ and $R^2$ are as defined above, to form the corresponding acetal. In the case of cyclic acetals, the alcohol must be a diol. Hereinafter, when the acetal is referred to, it will be understood that the corresponding precursors, i.e., the desired aldehyde and alcohol, are also intended to be included.

As mentioned above, the $R^1$ and $R^2$ substituents of the acetal may comprise a bridging group to form such cyclic acetals as

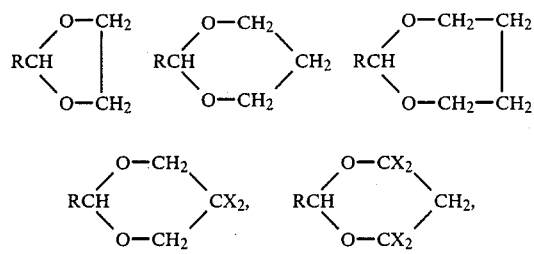

and the like, wherein R is defined above, and wherein X is selected from the group consisting of alkyl, aralkyl, aryl and cycloalkyl groups, preferably those having from 1 to 20 carbon atoms. As described above, cleavage of the ring under the conditions of this reaction will result in the formation of the corresponding hydroxy-substituted glycol ether.

Illustrations of products thus formed from cyclic acetals include, for example, diethylene glycol from dioxolane, the conversion of 2- or 4-methyldioxolane to the corresponding hydroxy glycol ether and the like.

It is important, in selecting the acetal starting material, that it not contain any substituents which would adversely affect the reaction. In other words, the R, $R^1$ and $R^2$ groups should not, for example, contain such reactive moieties as phosphine, arsine, amino, sulfido or carbonyl groups, acetal moieties, or olefins or acetylenic triple bonds. Other like groups will be recognized or readily determined by those skilled in the art as resulting in products other than the desired monoethers. On the other hand, halogen, alkoxy, and hydroxy moieties and the like may be present on the hydrocarbon substituents without adverse effect.

When these acetals are dealkoxyhydroxymethylated with syngas in accordance with the process of this invention, there is obtained the corresponding glycol monoether in which the ether moiety will correspond to the $R^1$ and $R^2$ groups of the acetal starting material. Also formed in lesser amounts are a tri-substituted ethane of the general formula

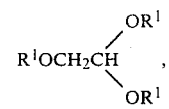

wherein $R^1$ (or, alternatively, $R^2$ or mixtures of $R^1$ and $R^2$) is as defined above, which may be recycled to form additional acetal starting material, and alcohol by-products. Again, as above, if the $R^1$ and $R^2$ groups of the acetal are different, a mixture of corresponding R-substituted compounds will result. This tri-substituted ethane is believed to form during the reaction from an alkoxyacetaldehyde, e.g., the intermediate methoxyacetaldehyde, when methylal is used, ethoxyacetaldehyde when ethylal is used, and the like.

As shown below, the selectivities for the desired monoether over the tri-substituted by-product are in the ratio of from about 3:1 to as much as 10:1 or more.

In a preferred embodiment of this invention, the starting materials are preferably symmetrical acetals where the $R^1$ and $R^2$ groups are lower alkyl groups of 1 to about 4 carbon atoms, thereby forming the corresponding ethylene glycol mono-lower alkyl ethers such as the monomethyl ether, the monoethyl ether, the monobutyl ether, and the like.

Alternatively, the acetal may contain such $R^1$ and $R^2$ groups as naphthyl and phenyl. In the case of naphthyl, the reaction, e.g., of the formaldehyde acetal with syngas will provide 2-(2-naphthyloxy) ethanol, a known sedative, which in turn may be oxidized to the corresponding 2-naphthyloxyacetic acid, a plant growth hormone.

Likewise, the dealkoxyhydroxymethylation of, e.g., the formaldehyde acetal wherein $R^1$ and $R^2$ are phenyl will produce 2-phenoxy-ethanol, a topical antiseptic, which when oxidized results in phenoxyacetic acid, a fungicide. Similarly, the formaldehyde acetal wherein $R^1$ and $R^2$ are 2,4,5-trichlorophenyl will yield 2,4,5-trichlorophenoxyacetic acid, an herbicide. In a like manner, when $R^1$ and $R^2$ are p-nonylphenyl, p-nonylphenoxyacetic acid, a corrosion inhibitor and antifoaming agent in gasoline and cutting oils will be formed.

Each of the aforedescribed products may be recovered routinely by methods will known in the art.

The invention will now be illustrated by, but is not intended to be limited to, the following examples.

EXAMPLES 1-6

A series of runs was carried out wherein 285 mmoles of methylal were reacted with various catalyst combinations, as shown in Table I below, in a closed reactor at 150° C. under 3000 psi of (2/1) syngas for 5 hours. As demonstrated by the results, the selectively to ethylene glycol monomethyl ether (EGMME), was significantly enhanced by the presence of the phosphite promoter.

TABLE I

METHYLAL DEALKOXYHYDROXYMETHYLATION[a]

| Example | CATALYST SYSTEM, (m moles) | | | YIELD OF EGMME[c] % | CONV. OF METHYLAL % |
|---|---|---|---|---|---|
| | [HCCo3(CO)9] | [Ru3(CO)12] | [P(O neo-C5H11)3][b] | | |
| 1 | 0 | 0 | 0 | 0 | 0 |
| 2 | 0.5 | 0 | 0 | 17 | 92 |
| 3 | 0.5 | 0.5 | 0 | 44 | 80 |
| 4 | 0.5[d] | 0.5 | 0 | 47 | 73 |
| 5 | 0.5 | 0.5 | 1.5 | 59 | 79 |
| 6 | 0.5[d] | 0.5 | 2.25 | 65 | 68 |

[a]285 mmoles of methylal reacted at 150° C. under 3000 psi of 2/1 syngas for 5 hours.
[b]Tri-neopentyl phosphite.
[c](Moles EGMME formed/moles methylal reacted) × 1000.
[d]Methylal dried over activated mole sieves before run.

EXAMPLES 7–20

A further series of runs was carried out wherein 4 mmoles of $Co_2(CO)_8$, 4 mmoles of $Ru_3(CO)_{12}$, tri-neopentyl phosphite and various solvents and reactants were charged together with butylal to a 300 ml autoclave, flushed 3 times with CO and $H_2$, brought to 3200 psig with a 1:1 mixture of CO and $H_2$ (syngas), heated to 150° C. and stirred for 3 hours at that temperature. Analysis was based on a standardized GLPC of the liquid product. The results are shown in Table II below.

EXAMPLES 21–32

In accordance with the general procedures of the foregoing examples, 70.6 mmoles of methylal, and 23.6 g. of o-dichlorobenzene, together with syngas (1:3 of $CO:H_2$) and various amounts of $HCCo_3(CO)_9$, $Ru_3(CO)_{12}$, and tri-cyclohexylphosphite were charged to an autoclave at a maximum pressure of 3100–3200 psi for 5–6 hours at 150° C. The results are shown in Table III below.

TABLE II

Effects of Solvents and Added Phosphite on Dealkoxyhydroxymethylation of Butylal to Form Ethylene Glycol Monobutyl Ether (DEMBE)

| Example | Solvent (ml) | CH2(OBu)2 (Ml) | (neo-C5H11O)3P (MMole) | GC Analysis of Reaction Mixture (Wt. %) | | | | |
|---|---|---|---|---|---|---|---|---|
| | | | | CH3OBu | PhCH3[b] | BuOH | CH2(OBu)2 | EGMBE[c] |
| 7 | None - 0 | 90 | 0 | 6.0 | 19.1 | 33.3 | 6.7 | 18.8 |
| 8 | None - 0 | 90 | 3 | 6.9 | 17.6 | 38.8 | 6.4 | 23.1 |
| 9 | n-BuOH - 45 | 45 | 0 | 2.5 | 17.2 | 61.6 | tr | 13.7 |
| 10 | n-BuOH - 67 | 23 | 0 | 0.9 | 16.4 | 73.8 | tr | 4.8 |
| 11 | n-BuOH - 45 | 45 | 3 | 1.9 | 14.5 | 63.0 | — | 17.0 |
| 12 | n-BuOH - 45 | 45 | 6 | 2.0 | 14.5 | 61.8 | tr | 16.6 |
| 13 | n-BuOH - 67 | 23 | 3 | 0.7 | 15.5 | 73 | | 8.4 |
| 14 | o-Cl2C6H4 - 67 | 23 | 0 | 0.9 | 18.0 | 5.7 | tr | 5.0 |
| 15 | o-Cl2C6H4 - 45 | 45 | 3 | 1.4 | 15.5 | 16.0 | 1.0 | 13.2 |
| 16 | o-Cl2C6H4 - 67 | 23 | 3 | 0.8 | 16.0 | 6.7 | 0 | 7.3 |
| 17 | o-Cl2C6H4 - 67 | 23 | 6 | 0.8 | 15.4 | 6.2 | 0 | 7.4 |
| 18 | PhCH3 - 45 | 45 | 3 | 7.9 | (7.8) | 14.1 | 3.2 | 12.9 |
| 19 | PhOCH3 - 67 | 23 | 6 | 0.6 | 13.2 | 6.4 | 0 | 6.7 |
| 20 | PhOCH3 - 45 | 45 | 3 | 2.0 | 14.1 | 15.8 | 0 | 14.8 |

| Example | GC Analysis of Reaction Mixture (Wt. %) | | | Conv. of CH2(OBu)2 (Mole %) | Select. To EGMBE (Mole %) | Yield of EGMBE (Mole %) |
|---|---|---|---|---|---|---|
| | TBE[d] | Unidentified Heavies | Solvent | | | |
| 7 | 4.3 | 7.3 | | 94 | 32 | 30 |
| 8 | 2.7 | 4.4 | | 94 | 43 | 40 |
| 9 | 3.2 | 1.8 | | >99 | 44 | 44 |
| 10 | 1.0 | 3.2 | | >99 | 28 | 28 |
| 11 | 1.0 | 1.5 | | >99 | 76 | 76 |
| 12 | 1.0 | 2 | | >99 | 72 | 72 |
| 13 | 0.3 | 1.2 | | >99 | 67 | 67 |
| 14 | 0.3 | 0.9 | 69.1 | 100 | 47 | 42 |
| 15 | 1.1 | tr | 51.9 | >97 | 68 | 70 |
| 16 | 0 | 0 | 69.1 | 100 | 76 | 76 |
| 17 | tr | tr | 67.5 | >99 | 81 | 81 |
| 18 | tr | tr | 58.6 | 92 | 64 | 58 |
| 19 | tr | tr | 72.4 | >99 | 70 | 70 |
| 20 | tr | tr | 53.2 | >99 | 71 | 71 |

[a]methoxybutane (by-product)
[b]toluene (added internal GC standard)
[c]EGMBE = ethylene glycol monobutylether
[d]tri-butoxyethane (by-product)

TABLE III

Phosphite-Promoted Dealkoxyhydroxymethylations of Methylal In the Presence of $HCCo_3(CO)_9$ and $Ru_3(CO)_{12}$

| EX-AMPLE | (a) | (b) | (c) | EGGME YIELD % | EGGME SELECT. % | METHYLAL CONV. % |
|---|---|---|---|---|---|---|
| 21 | .5 | 1.0 | 3.0 | 60 | 65 | 93 |
| 22 | .5 | .7 | 3.75 | 49 | 54 | 91 |
| 23 | .5 | .7 | 2.25 | 53 | 58 | 92 |
| 24 | .25 | .35 | 1.5 | 41 | 57 | 72 |
| 25 | .25 | .35 | 1.5 | 54 | 58 | 93 |
| 26 | .25 | .35 | 1.5 | 49 | 57 | 86 |
| 27 | .50 | 1.0 | 3.0 | 47 | 59 | 80 |
| 28 | .50 | .7 | 3.0 | 27 | 48 | 57 |
| 29 | .5 | .7 | 3.0 | 58 | 63 | 92 |
| 30 | .5 | 1.0 | 3.0 | 62 | 64 | 97 |
| 31 | .5 | 1.3 | 3.0 | 57 | 59 | 97 |
| 32 | 1.0 | 2.0 | 6.0 | 60 | 61 | 98 |

(a) $HCCo_3(CO)_9$, mmoles
(b) $Ru_3(CO)_{12}$, mmoles
(c) tri-cyclohexylphosphite, mmoles

EXAMPLE 33

In accordance with the procedures of Example 17 but substituting $RuCo_2(CO)_{11}$ for the 1:1 mixture of $Co_2(CO)_8$ and $Ru_3(CO)_{12}$, there are obtained high yields and selectivities of ethylene glycol monobutyl ether.

EXAMPLE 34

In accordance with the procedures of Example 6, but substituting $RuCo_2(CO)_{11}$ for the mixture of $HCCo_3(CO)_9$ and $Ru_3(CO)_{12}$, there are obtained high yields and selectivities of ethylene glycol monomethyl ether.

EXAMPLE 35

In accordance with the procedures of Example 34, but substituting the acetal diethoxymethane for methylal, one obtains high yields of ethylene glycol monoethyl ether.

EXAMPLE 36

In accordance with the procedures of Example 21, except that triphenyl phosphite is substituted for trineopentylphosphite, high yields of ethylene glycol monomethyl ether are obtained.

EXAMPLES 37-39

A series of runs was carried out in which the following general procedure was employed using as the catalyst $R^5CCo_3(CO)_9$, as shown in Table IV below, in combination with $Ru_3(CO)_{12}$ and tri-neopentylphosphite. $R^5$ was varied from hydrogen, to phenyl ($C_6H_5$—), to cyclooctenyl ($C_8H_{13}$—).

Reactions were carried out at 150° C. in a 110 ml rocker bomb with 25 ml of liquid charge and 800 psi CO/1600 psi $H_2$ added initially. After reaction, the mixture was analyzed by standardized gas chromatography.

TABLE IV

Methylal Dealkoxyhydroxymethylation[a]

| Example | Cobalt Complex | Ethylene Glycol Monomethyl Ether (Yield, Mole %) |
|---|---|---|
| 37 | $C_6H_5CCo_3(CO)_9$ | 45 |
| 38 | $HCCo_3(CO)_9$ | 42 |
| 39 | $C_8H_{13}CCo_3(CO)_9$ | 39 |

[a] $R^5CCo_3(CO)_9$, .5 mmoles; $Ru_3(CO)_{12}$, .5 mmoles; tri-neopentylphosphite, 0.75 mmoles; methylal, 25 ml; 800 psi CO; 1600 psi $H_2$; 150° C.; 5 hrs.

EXAMPLES 40-46

To a 110 ml rocking autoclave was charged the catalyst system, acetal, o-dichlorobenzene (23.55 gms.), mesitylene internal standard (1.18 gms.), and CO and $H_2$. The reaction mixture was heated to the temperature shown below, and rocked for the designated time. The reaction mixture was cooled and the liquid product analyzed by standardized gas chromotography. The results are shown in Table V below.

TABLE V

Dealkoxyhydroxymethylation of Formaldehyde Dialkyl Acetals

| Example | Cobalt Catalyst-mmoles | Ruthenium Catalyst-mmoles | Trialkyl Phosphite-mmoles | Acetal-mmoles |
|---|---|---|---|---|
| 40 | $HCCo_3(CO)_9$ - 0.5 | $Ru_3(CO)_{12}$ - 1.0 | Tricyclohexyl - 3.0 | $CH_2(OC_4H_9)_2$ - 32.8 |
| 41 | $HCCo_3(CO)_9$ - 0.5 | $Ru_3(CO)_{12}$ - 1.0 | Tricyclohexyl - 3.0 | $CH_2(OC_4H_9)_2$ - 32.8 |
| 42 | $HCCo_3(CO)_9$ - 0.5 | $Ru_3(CO)_{12}$ - 1.0 | Tricyclohexyl - 3.0 | $CH_2(OC_4H_9)_2$ - 32.8 |
| 43 | $HCCo_3(CO)_9$ - 0.5 | $Ru_3(CO)_{12}$ - 1.0 | Tricyclohexyl - 3.0 | $CH_2(OC_4H_9)_2$ - 32.8 |
| 44 | $HCCo_3(CO)_9$ - 0.5 | $Ru_3(CO)_{12}$ - 1.0 | Tricyclohexyl - 3.0 | $CH_2(OC_4H_9)_2$ - 32.8 |
| 45 | $HCCo_3(CO)_9$ - 0.5 | $Ru_3(CO)_{12}$ - 1.0 | Tricyclohexyl - 3.0 | $CH_2(OC_4H_9)_2$ - 50.6 |
| 46 | $HCCo_3(CO)_9$ - 0.5 | $Ru_3(CO)_{12}$ - 1.0 | Tricyclohexyl - 3.0 | $CH_2(OC_4H_9)_2$ - 50.6 |

| Example | Reaction Temp, °C. | Reaction Time, Min. | Init. CO. Pressure | Init. $H_2$ + CO Pressure | EGMBE[1] % Yield | EGMBE[1] % Selec. | EGMBE[1] % Conv. |
|---|---|---|---|---|---|---|---|
| 40 | 150 | 315 | 818 | 2417 | 85 | 85 | 100 |
| 41 | 150 | 300 | 819 | 2379 | 86 | 87 | 99 |
| 42 | 150 | 344 | 819 | 3207 | 92 | 97 | 95 |
| 43 | 150 | 465 | 820 | 3242 | 90 | 95 | 96 |
| 44 | 150 | 379 | 1215 | 2823 | 86 | 86 | 100 |
| 45 | 150 | 300 | 820 | 2395 | 82 | 82 | 99 |
| 46 | 125 | 215 | 821 | 2388 | 65 | 70 | 92 |

[1] EGMBE = ethylene glycol monobutyl ether

EXAMPLE 47

Using the procedures of Example 42 but substituting propionaldehyde dibutylacetal for formaldehyde dibutylacetal, the monobutyl ether of butylene glycol is produced in good yield.

EXAMPLE 48

Using the procedures of Example 47 but substituting acetaldehyde for propionaldehyde dibutylacetal and butanol for o-dichlorobenzene, the monobutyl ether of propylene glycol is produced in fair yield.

EXAMPLE 49

Using the procedures of Example 48 but substituting paraformaldehyde for acetaldehyde, the monobutyl ether of ethylene glycol is produced in fair yield.

EXAMPLES 50-54

To a 110 ml rocking autoclave was charged the catalyst system; acetal; o-dichlorobenzene (23.55 gms.); mesitylene internal standard (1.18 gms.); and CO and $H_2$. The reaction mixture was heated to the temperature shown below and rocked for the designated time. The reaction mixture was cooled and liquid product analyzed by standard gas chromotography. The results are shown in Table VI below.

TABLE VI
Dealkoxyhydroxymethylation of Acetaldehyde Diethyl Acetal

| Example | Cobalt Catalyst-mmoles | Ruthenium Promoter-mmoles | Trialkyl Phosphite-mmoles | Acetal-mmoles |
|---|---|---|---|---|
| 50 | $HCCO_3(CO)_9$ - 0.5 | $Ru_3(CO)_{12}$ - 1.0 | Tricyclohexyl - 3.0 | $CH_3CH(OC_2H_5)_2$ - 44.3 |
| 51 | $HCCO_3(CO)_9$ - 0.5 | $Ru_3(CO)_{12}$ - 1.0 | Tricyclohexyl - 3.0 | $CH_3CH(OC_2H_5)_2$ - 44.3 |
| 52 | $HCCO_3(CO)_9$ - 0.5 | $Ru_3(CO)_{12}$ - 1.0 | Tricyclohexyl - 3.0 | $CH_3CH(OC_2H_5)_2$ - 44.3 |
| 53 | $HCCO_3(CO)_9$ - 0.5 | $Ru_3(CO)_{12}$ - 1.0 | Tricyclohexyl - 3.0 | $CH_3CH(OC_2H_5)_2$ - 44.3 |
| 54 | $HCCO_3(CO)_9$ - 0.5 | $Ru_3(CO)_{12}$ - 1.0 | Tricyclohexyl - 3.0 | $CH_3CH(OC_2H_5)_2$ - 44.3 |

| Example | Reaction Temp, °C. | Reaction Time, Min. | Init. CO. Pressure | Init. $H_2$ + CO Pressure | PGMEE[b] % Yield | % Selec. | % Conv. |
|---|---|---|---|---|---|---|---|
| 50 | 150 | 330 | 816 | 2402 | 35 | 35 | 99 |
| 51 | 150 | 185 | 1616 | 3214 | 36 | 39 | 93 |
| 52 | 150 | 1070 | 819 | 3203 | 37 | 47 | 100 |
| 53 | 150 | 460 | 821 | 3209 | 47 | 49 | 100 |
| 54 | 150 | 290 | 812 | 3207 | 50 | 50 | 100 |

[a] A 300 ml rocking autoclave was use for this run.
[b] PGMEE = propylene glycol monoethyl ether.

EXAMPLES 55-57

To a 110 ml rocking autoclave was charged dicobalt octacarbonyl (0.5 mmoles), triruthenium dodecacarbonyl (1.0 mmole), a phosphite (3.0 mmoles), the acetal (27 mmole), the alcohol (18.2 ml), mesitylene as an internal standard, CO (800 psi), and $H_2$ to 3200 psi. The reaction mixture was heated to 150° C. and rocked for 6 hours, after which it was cooled and the liquid product analyzed by standarized GC. The results are reported in table VII below.

TABLE VII
Dealkoxyhydroxymethylation of Acetals in Alcohol Solvents

| Example | Phosphite | Acetal | Alcohol | Major Product | Yield % | Selec. % | Conv. % |
|---|---|---|---|---|---|---|---|
| 55 | (cyclo-$C_6H_{12}O)_3P$ | diethoxyethane | n-BuOH[a] | $CH_3CH(OBu)CH_2OH$ | (b) | (b) | (b) |
| 56 | (cyclo-$C_6H_{12}O)_3P$ | methylal | n-BuOH | $CH_2(OBu)CH_2OH$ | 59 | 59 | 99 |
| 57 | $(HO)_3P$ | methylal | n-BuOH | $CH_2(OBu)CH_2OH$ | 26 | 27 | 96 |

[a] n-butyl alcohol
[b] quantitative data unavailable

EXAMPLE 58

Following the procedures of Example 42 but substituting dibutylphosphite for tricyclohexyl phosphite, ethylene glycol monobutyl ether is obtained in excellent yield.

EXAMPLE 59

Following the procedures of Example 42 but substituting diethylphosphite for tricyclohexylphosphite, EGMBE is prepared in high yield.

EXAMPLE 60

Following the procedures of Example 54 but substituting dimethylphosphite for tricyclohexylphosphite there is obtained the monoethylether of propylene glycol in good yield.

EXAMPLE 61

Following the procedures of Example 5, except that the cyclic acetal dioxolane is used instead of methylal, diethylene glycol is produced as a reaction product.

EXAMPLE 62

Following the procedures of Example 5, but leaving out $Ru_3(CO)_{12}$, and substituting formaldehyde di-n-butyl acetal for methylal, there is obtained the corresponding monobutyl ether of ethylene glycol in good yield.

EXAMPLE 63

Following the procedures of Example 5, but substituting triruthenium undecacarbonyl (trineopentyl phosphite) for the ruthenium-component of the catalyst system employed therein, there is obtained ethylene glycol monomethyl ether.

EXAMPLE 64

Following the procedures of Example 5, but substituting methyne tricobalt octacarbonyl trineopentyl phosphite for the cobalt-component of the catalyst system employed therein, there is obtained ethylene glycol monomethyl ether.

What we claim is:
1. Composition consisting essentially of
(a) an organophosphite of the formula

$P(OR')_3$ wherein each of the R' groups, which may be the same or different, is hydrogen, alkyl, cycloakyl, or aryl; and (b) a ruthenium-cobalt carbonyl compound or mixture of ruthenium carbonyl and cobalt carbonyl compounds selected from the group consisting of:
(1) a mixture of $Co_2(CO)_8$ and $Ru_3(CO)_{12}$;
(2) $Co_2Ru(CO)_{11}$; and
(3) a mixture of $R^5CCo_3(CO)_9$ and $Ru_3(CO)_{12}$, wherein $R^5$ is hydrogen; alkyl; cycloalkyl or alkyl-substituted cycloalkyl; alkoxy; aryl or alkyl-, cyclo-alkyl-, alkoxy-, halo-, or cyano-substituted aryl; or a silyl moiety of the formula $R^6_3Si$, wherein $R^6$ is alkyl or aryl.

2. Composition of claim 1 wherein the phosphite is a trialkylphosphite, tricycloalkylphosphite or triarylphosphite.

3. Composition of claim 1 wherein the phosphite is a dialkylphosphite, dicycloalkylphosphite, or diarylphosphite.

4. Composition of claim 1 consisting essentially of $Co_2(CO)_8$, $Ru_3(CO)_{12}$, and $(neo-C_5H_{11}O)_3P$.

5. Composition of claim 1 consisting essentially of $Co_2(CO)_8$, $Ru_2(CO)_{12}$, and $(cyclo-C_6H_{12}O)_3P$.

6. Composition of claim 1 consisting essentially of $Co_2(CO)_8$, $Ru_3(CO)_{12}$, and $(n-C_4H_9O)_3P$.

7. Composition of claim 1 consisting essentially of $HCCo_3(CO)_9$, $Ru_3(CO)_{12}$, and $(neo-C_5H_{11}O)_3P$.

8. Composition of claim 1 consisting essentially of $HCCo_3(CO)_9$, $Ru_3(CO)_{12}$, and $(cyclo-C_6H_{12}O)_3P$.

9. Composition of claim 1 consisting essentially of $HCCo_3(CO)_9$, $Ru_3(CO)_{12}$, and $(n-C_4H_9O)_3P$.

10. Composition of claim 1 consisting essentially of $Co_2(CO)_8$, $Ru_3(CO)_{12}$, and dimethylphosphite.

11. Composition of claim 1 consisting essentially of $Co_2(CO)_8$, $Ru_3(CO)_{12}$, and diethylphosphite.

12. Composition of claim 1 consisting essentially of $PhCCo(CO)_9$, $Ru_3(CO)_{12}$, and $(neo-C_5H_{11}O_3)_3P$, wherein Ph is phenyl.

13. Composition of claim 1 consisting essentially of $CH_3CCo(CO)_9$, $Ru_3(CO)_{12}$, and $(cyclo-C_6H_{12}O)_3P$.

14. Composition of claim 1 consisting essentially of $cyclo-C_8H_{13}CCo(CO)_9$, $Ru_3(CO)_{12}$, and $(n-C_4H_9OO_3P$.

15. Composition consisting essentially of
(a) an organophoshite of the formula $P(OR')_3$ wherein each of the R' groups, which may be the same or different, is hydrogen, alkyl, cycloalkyl, or aryl; and (b) a cobalt carbonyl compound of the formula $R^5CCo_3(CO)_9$ wherein $R^5$ is hydrogen; alkyl; cycloalkyl or alkyl-substituted cycloalkyl; cycloalkenyl; alkoxy; aryl or alkyl-, cycloalkyl-, alkoxy-, halo-, or cyano-substituted aryl; or a silyl moiety of the formula $R^6_3Si$, wherein $R^6$ is alkyl or aryl.

16. Composition of claim 15 wherein the phosphite is a trialkylphosphite, tricycloalkylphosphites or triarylphosphite.

17. Composition of claim 15 wherein the phosphite is a dialkylphosphite, dicycloalkylphosphite, or diarylphosphite.

18. Composition of claim 15 consisting essentially of $HCCo_3(CO)_9$, and $(neo-C_5H_{11}O)_3P$.

19. Composition of claim 15 consisting essentially of $HCCo_3(CO)_9$, and $(cyclo-C_6H_{12}O)_3P$.

20. Composition of claim 15 consisting essentially of $HCCo_3(CO)_9$, and $(n-C_4H_9O)_3P$.

21. Composition of claim 15 consisting essentially of $PhCCo(CO)_9$, and $(neo-C_5H_{11}O_3)_3P$, wherein Ph is phenyl.

22. Composition of claim 15 consisting essentially of $CH_3CCo(CO)_9$, and $(cyclo-C_6H_{12}O)_3P$.

23. Composition of claim 15 consisting essentially of $cyclo-C_8H_{13}CCo(CO)_9$, and $(n-C_4H_9O)_3P$.

24. The composition $R^5CCo_3(CO)_{9-x}(P(OR')_3)_x$;

wherein each of the R' groups, which may be the same or different, is hydrogen, alkyl, cycloalkyl, or aryl; and wherein $R^5$ is hydrogen, alkyl, cycloalkyl or alkyl-substituted cycloalkyl; cycloalkenyl; alkoxy; aryl or alkyl-, cycloalkyl-, alkoxy-, halo-, or cyano-substituted aryl; or a silyl moiety of the formula $R^6_3Si$, wherein $R^6$ is alkyl or aryl; and wherein x is an integer of from 1–3 inclusive.

* * * * *